United States Patent [19]
Ichikawa et al.

[11] Patent Number: 5,788,831
[45] Date of Patent: Aug. 4, 1998

[54] METHOD FOR STERILIZING APPARATUS FOR PREPARATION OF RECORDING MATERIAL

[75] Inventors: Yasunori Ichikawa; Yoshihisa Noguchi; Masanori Abe; Mika Nishiguchi, all of Kanagawa, Japan

[73] Assignee: Fuji Photo Film Co., Ltd., Kanagawa, Japan

[21] Appl. No.: 916,220

[22] Filed: Aug. 22, 1997

Related U.S. Application Data

[63] Continuation of Ser. No. 532,975, Sep. 22, 1995, abandoned.

[30] Foreign Application Priority Data

Oct. 12, 1994 [JP] Japan .................. 6-271830

[51] Int. Cl.⁶ .................................................. C02F 1/461
[52] U.S. Cl. .......................... 205/701; 205/742; 205/746; 134/3
[58] Field of Search .......................... 205/701, 742; 134/3

[56] References Cited

U.S. PATENT DOCUMENTS

| | | | |
|---|---|---|---|
| 4,710,233 | 12/1987 | Hohmann et al. | 205/701 |
| 5,051,161 | 9/1991 | Yamaguchi et al. | 204/229 |
| 5,256,268 | 10/1993 | Goto et al. | 204/268 |
| 5,445,722 | 8/1995 | Yamaguchi et al. | 204/229 |
| 5,474,662 | 12/1995 | Miyamae | 204/257 |

FOREIGN PATENT DOCUMENTS 60-131532  7/1985  Japan .

*Primary Examiner*—Arun S. Phasge
*Attorney, Agent, or Firm*—Sughrue, Mion, Zinn, Macpeak & Seas, PLLC

[57] ABSTRACT

An inexpensive, safe method for sterilizing an apparatus for the preparation of a recording material, which obviates troubles affecting a coated surface of the recording material caused by bacteria and fungi, does not cause changes in photographic performance (sensitivity, fog, graininess and sharpness), can prevent the appearance of "resistant cells", and can comply with environmental problems, said method comprising sterilizing a surface of the apparatus being in contact with a coating composition for the recording material by use of a strongly acidic solution having a redox potential of 1,000 mV or more which is obtained by electrolysis of water.

7 Claims, 2 Drawing Sheets

METHOD FOR STERILIZING APPARATUS FOR PREPARATION OF RECORDING MATERIAL

This is a continuation of application Ser. No. 08/532,975 filed Sep. 22, 1995, now abandoned.

FIELD OF THE INVENTION

The present invention relates to a method for washing, and sterilizing an apparatus for the preparation of a recording material, particularly an apparatus for preparing a silver halide emulsion, a coupler emulsified product or a photographic emulsion, which is a photographic material, an apparatus for preparing a coating solution using the above-mentioned respective emulsions, an apparatus for transferring the above-mentioned coating solution, or an apparatus for transferring a liquid while adding a chemical agent or chemical agents thereto and mixing them, particularly from the viewpoint of microorganisms.

BACKGROUND OF THE INVENTION

Apparatuses for preparing silver halide photographic emulsions have hitherto been required to be washed to an extremely severe degree. For example, even contamination with the same kind of silver halide photographic emulsion has been known to significantly affect the photographic performance. The washing methods which have previously been used include the method of washing by spraying hot water having a temperature of 50° to 80° C. at a high pressure of 10 to 100 kg/cm$^2$ through a so-called spray ball, and the method of scrubbing a surface of a container, etc. by rotation of a brush. However, the container is not sufficiently washed because the high-pressure hot water does not strike some portions or the brush does not reach them. These methods are called "physical washing methods", and described in JP-B-59-2015 (the term "JP-B" as used herein means an "examined Japanese patent publication"), JP-A-62-125890 (the term "JP-A" as used herein means an "unexamined Japanese patent publication), and JP-A-2-86681.

In order to solve this problem, the methods of using chemical solutions as washing solutions are proposed.

(1) As washing solutions reacting with silver halides, substances forming complex compounds high in solubility by chemical reaction are used. The substances generally forming the complex compounds with the silver halides to dissolve the silver halides include substances containing divalent anions such as $SO_3^{2-}$ and $S_2O_3^{2-}$, and inorganic salts containing univalent anions such as Br$^-$, I$^-$, CN$^-$, SCN$^-$ and SeCN$^-$. Of these, the I-containing inorganic salts (for example, KI and NaI) can be expected to show a good effect. The concentration of I is within the range of 1N to 8N (saturation density) (see JP-A-59-49534, JP-B-02-7451 and JP-A-06-82940).

(2) Then, a method is proposed in which substances forming complex compounds high in solubility by chemical reaction with silver halides and substances decomposing gelatin to increase solubility are used in combination as detergents. It is possible to wash off stains of the silver halides, but it is impossible to wash off gelatin which has adhered to apparatuses for the preparation of emulsions, even with high-pressure hot water of 100 kg/cm$^2$ and 80° C. Acids, alkalis, proteinases, etc. are therefore used as the substances decomposing gelatin to increase the solubility, and the alkalis are preferably used among others. This is a reason why this method is used. The alkalis suitably used as the substances decomposing gelatin to increase the solubility include NaOH, KOH, Ca(OH)$_2$ and NH$_4$OH, and the concentration thereof is about 0.1N to 1N (see JP-A-59-188638, JP-A-1-262539, JP-B-2-7451, JP-A-2-262639, JP-A-5-61139, JP-A-6-82939 and JP-A-6-82940).

(3) For completely removing gelatin films, for example, use of a solution of silica gel in sodium hypochlorite as a detergent in which silica gel is dissolved in a washing solution is also disclosed in JP-A-63-120798.

(4) Further, the apparatuses for the preparation of the photographic materials are very complicated. One photographic material has ten and several layers when many layers are formed. For the purpose of deriving the photographic characteristics of each layer or ensuring the liquid characteristics in preparing, various chemical agents are added to each layer. The apparatus is therefore made up of a plurality of tanks such as tanks for preparing chemical solutions, storage tanks, metering devices and mixing tanks, and pipes which connect them. It is further provided with various supervisory instruments and controllers, thus resulting in a complicated structure. Such an apparatus has usually been washed by the physical washing methods (brush washing, high-pressure washing, etc.) described in (1), (2) and (3) shown above, washing with hot water and washing with chemical solutions (acids, alkalis, etc.). However, the apparatus is not necessarily completely washed, because it is provided with the various devices and instruments as described above. Gelatin or various chemical agents are left on such incompletely washed portions, and become nutrient sources for microorganisms to easily form hotbeds in which bacteria and fungi propagate. In order to solve this problem, inhibition of generation of bacteria and fungi by use of preservatives with respect to photographic materials is described in JP-A-59-91440, JP-A-59-226343, JP-A-60-186836, JP-A-2-32337, JP-A-2-287535, JP-A-3-130759 and JP-A-3-59552. However, only JP-A-60-131532 mainly aims at sterilization of the apparatus when it is washed.

JP-A-60-131532, entitled "Method for Sterilizing Apparatus for Preparation of Silver Halide Photographic Material", discloses a method for sterilizing an apparatus for the preparation of a silver halide photographic material which comprises treating the apparatus with an aqueous solution containing a compound represented by the following general formula:

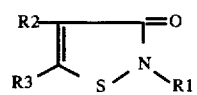

wherein R1 represents a hydrogen atom, an alkyl group, a cyclic alkyl group, an alkenyl group, an aralkyl group, an aryl group, a heterocyclic group, an alkylamido group, an arylamido group, an alkylthioamido group, an arylthioamido group or an arylsulfoamido group; and R2 and R3 each represents a hydrogen atom, a halogen atom, an alkyl group, a cyclic alkyl group, a cyano group, an alkylthio group, an arylthio group, an alkylsulfoxy group, an alkylsulfonyl group or a heterocyclic group.

However, this method has the following disadvantages:

(1) When pipes, etc. are washed, immersion thereof for a certain period of time (1 hour in the example) is required to exhibit the sterilization effect.

(2) As described in the example, although the effect of inhibiting bacteria is observed, it is impossible to completely sterilize bacteria in a system (a level at which 1,000 cells are reduced to 10 cells).

(3) Many chances to contact with the same chemical agents produce "resistant cells" as the ecological characteristics of bacteria, unless the bacteria are allowed to become completely extinct, resulting in disappearance of the effect of adding the chemical solutions unawares.

(4) The photographic materials are sensitively reacted with various chemical agents to change their photographic performance in many cases. There is no problem in the system in which the performance is evaluated as described in the example. However, when current products are switched to new products into which novel materials are incorporated, it is very troublesome to evaluate the influence of the chemical solutions on the photographic performance.

(5) Addition of specified amounts of the chemical solutions to the washing solutions and constant maintenance under uniform conditions necessitate expensive equipment and troublesome control.

(6) Use of the chemical solutions for the purpose of removing bacteria and fungi adhering to the apparatuses causes an increase in cost.

(7) When washing discharges contain the chemical solutions for the purpose of killing bacteria and fungi, equipment used in a step in which the discharges are treated is required to comply therewith. In particular, the photographic treatment discharges contain gelatin, etc., so that the activated sludge process is frequently employed. However, the discharges containing the chemical solutions make such a process impossible.

(8) Use of the chemical solutions which kill microorganism in water must be restrained to the utmost, considering recent world-wide attention to environmental problems.

SUMMARY OF THE INVENTION

It is therefore a principal object of the present invention to provide a method for sterilizing an apparatus for the preparation of a photographic material, by which contamination of the apparatus with microorganisms is prevented, in order to obviate troubles affecting a coated surface such as comet and repelled spot caused by bacteria and fungi.

Another object of the present invention is to provide a method for sterilizing an apparatus for the preparation of a photographic material, which does not cause changes in photographic performance (sensitivity, fog, graininess and sharpness) which are produced at the time of use of a preservative and a fungicide.

A still another object of the present invention is to provide a method for sterilizing an apparatus for the preparation of a photographic material, which can prevent the appearance of "resistant cells" observed in sterilization using various compounds.

A further object of the present invention is to provide an inexpensive, safe method for sterilizing an apparatus for the preparation of a photographic material, which can comply with environmental problems to which worldwide attention is now given.

According to the present invention, there are provided (1) a method for sterilizing an apparatus for the preparation of a recording material, which comprises sterilizing a surface of the apparatus being in contact with a coating composition for the recording material by use of a strongly acidic solution having a redox potential of 1,000 mV or more which is obtained by electrolysis of water, and (2) the method described in (1), wherein the recording material is a photographic material.

DETAILED DESCRIPTION OF THE INVENTION

In the present invention, the surface of the apparatus being in contact with the coating composition for the recording material means surfaces of tanks for preparing chemical solutions, metering devices and pipes which connect them, said surfaces being in contact with the chemical solutions.

As water used in the present invention, tap water, well water and industrial water can be used in some cases. However, it is preferred to use pure water (distilled water or ion-exchanged water) which is not contaminated by an ion component unfavorable for photographic preparation and can prolong the life of electrodes. When such pure water is used, an appropriate amount of NaCl or KCl may be added to facilitate electrolysis.

The strongly acidic solution used in the present invention is obtained, for example, by the method and device described in JP-A-1-317591. That is to say, two electrolytic baths are formed, each bath divided into an anode chamber and a cathode chamber by partitioning the bath with a diaphragm between an anode and a cathode. Water to be treated is supplied to the anode chamber and the cathode chamber of the first electrolytic bath, and then, water treated in the respective chambers is supplied to the reverse polar chambers of the second electrolytic bath, respectively, thereby obtaining the strongly acidic solution. In addition to "Oxilyzer" developed by Miura Denshi Co., such devices are available from Nippon Index Co. Ltd., Nippon Janix Co. Ltd., Corona Kogyo Co. Ltd., Omron Electronics Co., Hoshizaki Denshi Co. Ltd., Asahi Engineer Co. Ltd., The Japan Carlit Co., Ltd. and Hirata Corporation. A solution having a redox potential of 1,000 mV or more produced from the side of the second anode chamber is used as the washing solution.

In the case of the present invention, it is possible to allow sterilization to be compatible with washing by using the strongly acidic electrolyte which is electrically treated and can instantaneously sterilize microorganisms such as bacteria and fungi remaining on incompletely washed portions as described above, adjusting the acidic electrolyte to the characteristics of the apparatus, for example, by using the heated strongly acidic electrolyte as a high-pressure washing solution when a tank is washed, or by bubbling pressurized air into the strongly acidic electrolyte when a pipe is washed. After washing with the chemical solution, rinsing with pure water is usually carried out. However, it is also possible to conduct rinsing and sterilization at the same time using the strongly acidic electrolyte instead of pure water.

Figure 1:
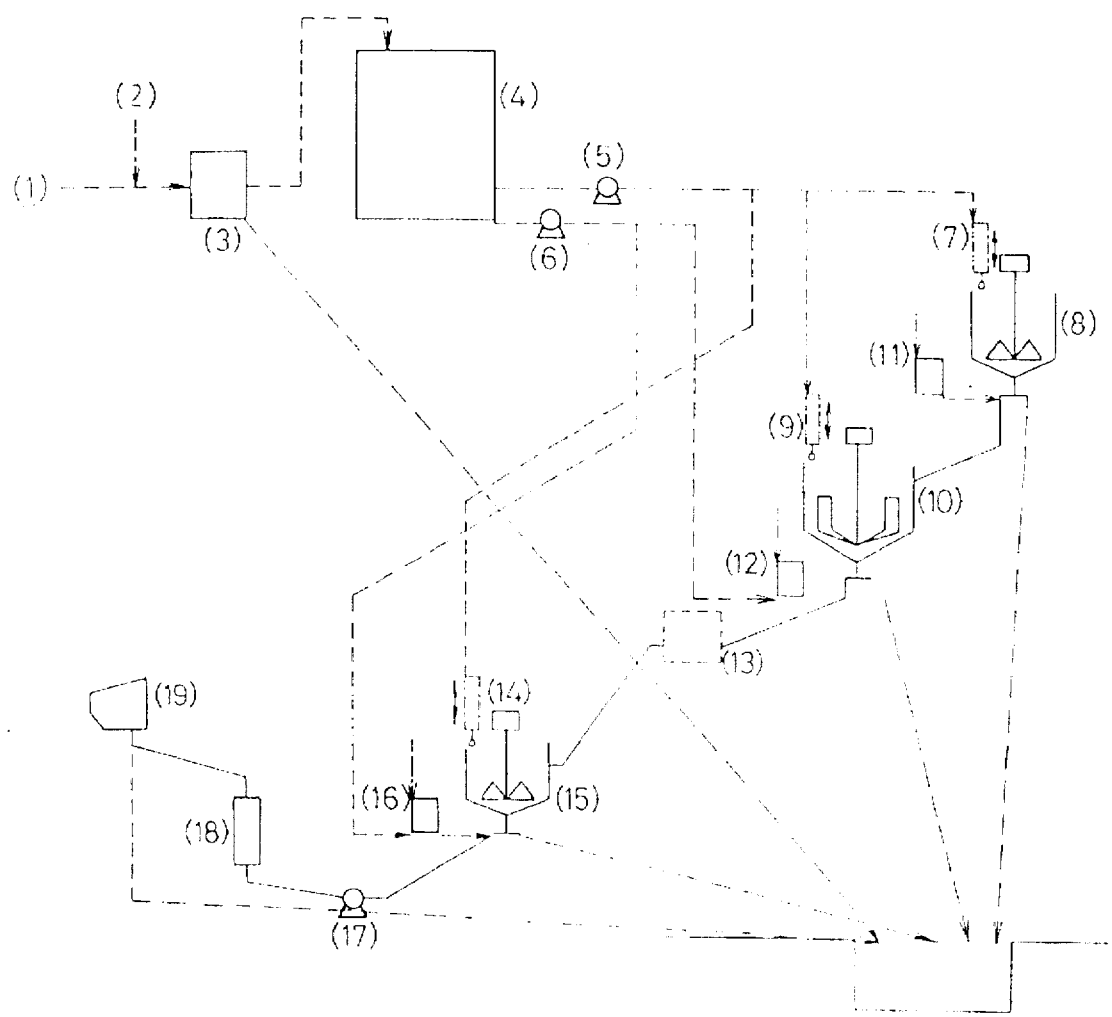
FIG. 1 is a flow sheet showing one embodiment of an apparatus used for performing a method of the present invention.

FIG. 1 is a schematic view showing one embodiment of an apparatus used for conducting the present invention.

Referring to FIG. 1, the reference numeral 3 designates a device for preparing a strongly acidic electrolyte, the reference numeral 1 designates water to be electrolyzed, and the reference numeral 2 designates a salt (NaCl or KCl) added as an electrolyte. The device 1 is an Oxilyzer developed by Miura Denshi Co., Ltd. Washing water used herein is a solution having a redox potential of 1,000 mV or more produced from the side of an anode, and the device 1 is not particularly limited to the device supplied from the above-mentioned maker. In such a device, tap water, well water or industrial water is generally used. However, when this device is used for photographic preparation, it is preferred that pure water (distilled water or ion-exchanged water) is used as water designated by 1. The reason for this is that use of tap water, well water or industrial water for the preparation of the strongly acidic electrolyte brings about contamination by ion components such as $Ca^{++}$ and $Mg^{++}$ unfavorable for photographic preparation, which exerts an influence on the photographic performance or shortens the life of electrodes, resulting in failing to obtain the desired performance, when a large amount of solution is intended to be secured.

Referring to FIG. 1, the reference numeral 8 designates a tank for preparing a chemical agent used for the preparation of a photographic material, in which a pH regulator, an antifogging agent, a surface active agent, a thickener, a photographic sensitivity regulator, a silver halide emulsion solution, a coupler emulsion for color image formation or a gelatin solution is prepared and dissolved. The reference numeral 10 designates a stock tank for supplying the various chemical solutions prepared and dissolved in the above-mentioned tank 8 to the next stage. Further, the reference numeral 13 designates an instrument for metering the stocked chemical solution. In addition to various types of flowmeters (such as an electromagnetic flowmeter, an oval flowmeter, a Coriolis type mass flowmeter, an ultrasonic flowmeter and a turbine flowmeter), use of metering tank systems (such as a load cell system, a level meter systems (such as an electrode system, a float system or a capacitance system), a differential pressure transmission system and an ultrasonic level detection system) is known. Then, the reference numeral 15 designates a tank for preparing a coating solution by mixing various chemical agents. The coating solution is transferred to a giezer 19 at which the coating solution is applied, through a defoaming means 18, etc. by a pump 17, a liquid transfer means, and applied thereat. Although not shown in FIG. 1, temperature sensors, filters and instruments for measuring liquid properties such as pH, viscosity, electric conductivity and specific gravity are arranged between the tanks and between the tank 15 and the giezer 19 as so desired to form such a complicated structure that it can not be indicated in the drawing. The reference numerals 7, 9 and 14 each designate high-pressure washing devices for washing the respective tanks, and the reference numeral 5 designates a high-pressure pump for sending the strongly acidic electrolyte into the tanks at a pressure of 3 $kg/cm^2$ to 150 $kg/cm^2$. Although automatic rise-and-fall type spray balls are used as the high-pressure washing devices in FIG. 1, they are only one embodiment of tank washing systems.

Further, pressurized air is introduced into the strongly acidic electrolyte supplied from a booster pump 6 (pressure: 1 $kg/cm^2$ to 30 $kg/cm^2$), by use of devices 11, 12 and 16 to prepare a supersaturated strongly acidic electrolyte, and the air is released in pipes to conduct bubbling washing. Fine bubbles may be previously introduced into the strongly acidic electrolyte by use of the devices 11, 12 and 16 to conduct bubbling washing. Practically, the devices 11, 12 and 16 are not necessarily required. When these devices are not used, the strongly acidic electrolyte is allowed to flow in the pipes under the conditions that the strongly acidic electrolyte in the pipes shows a Reynolds number of 100,000 or more, preferably 150,000 or more.

In the preparation process of the photographic material, an aqueous solution of gelatin is generally used as a binder. The gelatin solution shows the gel state at a temperature of 20° C. or less and the sol state at a temperature of higher than 20° C. although it depends on the concentration thereof. In many cases, therefore, the gelatin solution is usually used at a temperature of 25° C. to 45° C. Such a temperature corresponds to the optimum growth temperature for bacteria, so that bacteria actively propagate consuming gelatin and various chemical agents as nutrient sources. Some of such bacteria produce enzymes which decompose gelatin, etc., and the enzymes destroy the molecular structure thereof to induce a reduction in viscosity, which causes troubles such as deterioration in coating property. Further, generation of the aggregates due to dead bacteria or products thereof causes generation of comet and repelled spot.

Using Pseudomonas and Enterobacter as typical strains of such bacteria, the following tests were conducted.

EXAMPLE 1 AND COMPARATIVE EXAMPLE 1

Using a compound (shown below) described in JP-A-60-131532 and a strongly acidic electrolyte (having a redox potential of 1100 mV) of the present invention, the sterilization ability was compared for bacteria existing on pipe packings when washing was completed.

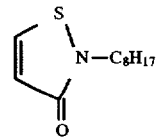

(Compound described in JP-A-60-131532)

Figure 2:
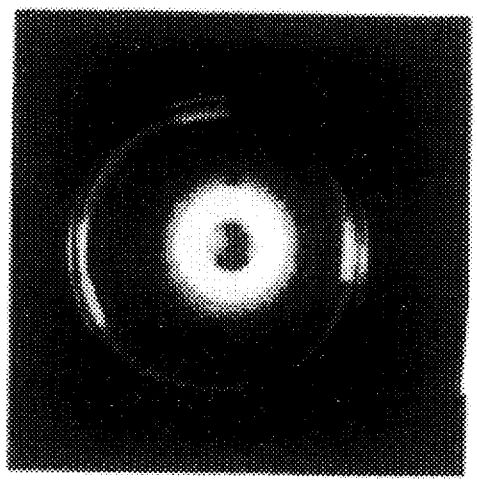
FIG. 2 is a photograph showing a result of a culture test of bacteria on a Teflon packing used in a joint portion when a microbicide described in JP-A-60-131532 is used as a comparative example.
Figure 3:
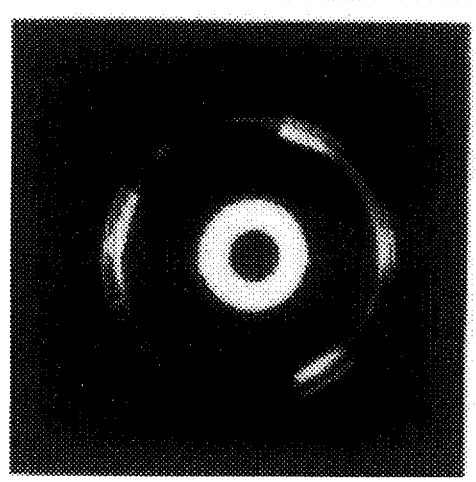
FIG. 3 is a photograph showing a result of a culture test of bacteria on a Teflon packing used in a joint portion when a strongly acidic electrolyte of the present invention is used as a microbicide.

In this test, pipes between tanks were provided with five ferrule joint units which meet the sanitary standards, and the pipes were immersed in a solution for 24 hours which prepared by adding Pseudomonas to an aqueous solution of gelatin previously prepared and diluting so as to give a cell number of 10,000 cells/ml. At this time, the pipe temperature was kept at 35° C. After this solution was discarded, the pipes were washed with the strongly acidic electrolyte (having a redox potential of 1100 mV) of the present invention at 50° C., followed by repeated pipe immersion test in the above-mentioned electrolyte solution for 5 minutes, 30 minutes and 60 minutes (Example 1). The test was repeated in the same manner as with Example 1 with the exception that the strongly acidic electrolyte was substituted by a solution prepared by adding 0.0001% of the above-mentioned compound shown in JP-A-60-131532 to hot water heated at 50° C. (Comparative Example 1). After the termination of this test, the pipes were disassembled to take out the Teflon packings used in the joint units. The packings were each placed on dishes for testing bacteria, and a specified amount of culture medium for general bacteria which was previously prepared was poured therein to conduct a culture test. Of these results, typical photographs are shown in FIG. 2 for Comparative Example 1, and in FIG. 3 for Example 1. The test results are also shown in Table 1 by evaluation of marks: ○, ∆, and ×.

TABLE 1

|  | Bacterium Test Results | | |
| --- | --- | --- | --- |
|  | 5 min | 30 min | 60 min |
| Comparative Example 1 (Method described in JP-A-60-131532) | x | x | x–∆ |
| Example 1 (Invention) | ∆–○ | ○ | ○ |

Note: ○: Good, ∆: Fair, x: Poor

As can be easily appreciated from these results, it is apparent that the strongly acidic electrolyte used in the present invention penetrates a structure such as the pipe packing for a short period of time to provide a very effective sterilization effect.

EXAMPLE 2

In order to examine the state of an inner surface of a tank with regard to adhesion of bacteria, 80 liters of an aqueous solution of gelatin sterilized in an autoclave was placed in the tank 10 in FIG. 1, and Enterobacter (about 100,000 cells/ml) was added thereto, followed by standing at 35° C. for 24 hours. At this time, the number of cells was about 10,000,000 cells/ml. After this aqueous solution of gelatin was discarded, a strongly acidic electrolyte (having a redox potential of 1180 mV and a temperature of 40° C.) of the present invention was sprayed through a spray ball at a pressure of 5 kg/cm$^2$ at a flow rate of 30 liters/minute. Previously defining a locus of the spray ball, the relationship between the spray time and the number of bacteria adhering to the wall surface was examined in detail. As levels of the spray time, 1 minute, 2.5 minutes, 5 minutes, 7.5 minute and 10 minutes were established. Food stamps for general bacteria were used for the bacterium test. Three data were collected from different places for each level, and an average thereof was determined by visual evaluation using marks ○, △, and ×. In the case of food stamps, the decision was carried out as ×: numerous, △: 1–100 cells, and ○: not detected, because of difficulty of quantitative evaluation.

Further, the degree of washing was evaluated by reading the concentration of a solution discharged from the tank from a calibration curve previously prepared using a spectrophoto-meter (detection limit: 0.1 ppm).

The results thereof are shown in Table 2.

TABLE 2

|  | Elapsed Time | | | | |
| --- | --- | --- | --- | --- | --- |
|  | 1.0 min | 2.5 min | 5.9 min | 7.5 min | 10 min |
| Concentration (%) | 80 | 3 | 0.5 | 0.1↓ | 0.1↓ |
| Detection of Bacteria | x | △–○ | ○ | ○ | ○ |

Note: ○: Not detected, △: 1–100 cells, x: Numerous

These results apparently reveal that the bacteria contained in gelatin adhering to the wall surface are sterilized by washing with a large amount of strongly acidic electrolyte before complete removal of gelatin by washing, which results in compatibility of washing and sterilization.

EXAMPLE 3 AND COMPARATIVE EXAMPLE 2

A strongly acidic electrolyte was added to 100 g of silver chlorobromide (containing 0.06 mol of silver and 10 g of gelatin) containing 30 mol % of silver bromide subjected to sulfur sensitization and gold sensitization under the following conditions to examine the effect of the strongly acidic electrolyte on the photographic performance. The amount of liquid remaining in a pipe (the deposit in the pipe) after washing was calculated by a preliminary test, which revealed that the concentration was about 0.1% when it was assumed that a solution transferred brought all the deposit in the inside on batch production.

Based on this concentration, the strongly acidic electrolyte is forcedly added to the following samples:

Sample 1: No addition of the strongly acidic electrolyte (Comparative Example 1)

Sample 2: Addition of 0.1% by weight of the strongly acidic electrolyte

Sample 3: Addition of 0.5% by weight of the strongly acidic electrolyte

Sample 4: Addition of 1.0% by weight of the strongly acidic electrolyte

Sample 5: Addition of 5.0% by weight of the strongly acidic electrolyte (Example 3)

The emulsion was applied to a transparent cellulose triacetate support to give an amount of silver applied of 2.0 g/m$^2$.

This sample was exposed using a tungsten light source having a color temperature of 2854° K. through a silver wedge for 1/50 second, followed by development with an LD-835 developing solution manufactured by Fuji Photo Film Co., Ltd. at 20° C. for 6 minutes. Then, fixing, washing and drying were normally conducted, and the density was measured with a Fuji automatic densitometer to compare the evaluation of the photographic performance. The results thereof are shown in Table 3. Although each datum was indicated by an average value of three levels, the variation in data was very small.

TABLE 3

| Sample No. | Concentration of Strongly Acidic Electrolyte Added (%) | Sensitivity | Gamma | Fog |
| --- | --- | --- | --- | --- |
| 1 | 0 | 1.149 | 2.929 | 0.10 |
| 2 | 0.1 | 1.150 | 2.928 | 0.10 |
| 3 | 0.5 | 1.149 | 2.930 | 0.10 |
| 4 | 1.0 | 1.151 | 2.929 | 0.10 |
| 5 | 5.0 | 1.149 | 2.930 | 0.10 |

These results reveal that direct addition of a 50-fold excess of the amount of liquid remaining in the pipe after washing to the emulsion has no influence on the photographic performance at all.

As is shown in Example 3, use of the strongly acidic electrolyte in place of water does not possibly cause changes in performance. However, it is known that the influence slightly varies according to the kind of chemical agent. Most of the chemical agents do not raise problems, but some of them cause changes in performance with time.

(1) With respect to washing and sterilization in the photographic preparation stages, washing for removing contaminants has previously been conducted, followed treatment with microbicides. According to the present invention, however, it is possible to conduct washing and sterilization at the same time to obviate troubles of products. A spray ball or a brush is not necessarily required for washing, and any washing device may be used.

(2) Water drain similar to that of normal washing has no influence on the photographic performance at all, even if photographic materials are contaminated by remaining water drops.

(3) When preservative treatment and sterilization are carried out using chemical solutions, the effect is lost by use thereof for a long period of time because of the appearance of resistant cells. In the case of the strongly acidic electrolytes, however, the appearance of resistant cells is not observed, and the effect is maintained.

(4) When microbicides or preservatives are used in washing, these chemical solutions flow in a waste water treatment stage, which makes it difficult to conduct waste water treatment, particularly the activated sludge process generally employed in sewage treatment. Accordingly, there has been fear of environmental contamination. However, the influence on activated sludge can be completely eliminated by mixing strongly basic solutions obtained as by-products when the strongly acidic electrolytes are produced, with waste water, and the chemical solutions can be used without anxiety.

While the invention has been described in detail and with reference to specific embodiments thereof, it will be apparent to one skilled in the art that various changes and modifications can be made therein without departing from the spirit and scope thereof.

What is claimed is:

1. A method of sterilizing an apparatus used for the preparation of a recording material, comprising contacting a surface of the apparatus adapted to be in contact with a coating composition for the recording material, with a strongly acidic solution comprising electrolyzed water and having a redox potential of 1,000 mV or more.

2. The method as claimed in claim 1, wherein the recording material is a photographic material.

3. The method as claimed in claim 1, wherein said strongly acidic solution is made from pure water.

4. The method as claimed in claim 3, wherein said pure water is distilled water or ion-exchanged water.

5. The method as claimed in claim 3, wherein an appropriate amount of NaCl or KCl is added to the pure water.

6. The method as claimed in claim 4, wherein an appropriate amount of NaCl or KCl is added to the pure water.

7. The method as claimed in claim 1, wherein the electrolyzed water is obtained by electrolysis of water in two electrolytic baths that are divided into an anode chamber and a cathode chamber by partitioning the bath with a diaphragm.

* * * * *